US00PP09198P

United States Patent [19]

van der Kooy

[11] Patent Number: Plant 9,198

[45] Date of Patent: Jul. 18, 1995

[54] HYBRID TEA ROSE PLANT NAMED 'RUIKOOWI'

[75] Inventor: W. M. van der Kooy, EB Zevenhuizen, Netherlands

[73] Assignee: DeRuiter's Nieuwe Rozen, B.V., Hazerwoude, Netherlands

[21] Appl. No.: 188,132

[22] Filed: Jan. 25, 1994

[51] Int. Cl.[6] ..... A01H 5/00

[52] U.S. Cl. ..... Plt./11

[58] Field of Search ..... Plt. 11, 12, 18, 19

*Primary Examiner*—Howard J. Locker

*Attorney, Agent, or Firm*—Christie, Parker & Hale

[57] ABSTRACT

A new variety of hybrid tea rose plant having pink blend flowers and suitable for growing under glass.

2 Drawing Sheets

SUMMARY OF THE INVENTION

The present invention relates to a new and distinct variety of rose plant of the hybrid tea rose class which was discovered as a naturally occurring mutation in a controlled planting of the variety 'Ruidriko', U.S. Plant Pat. No. 7,362. The varietal denomination of the new variety is 'Ruikoowi'. The new variety was isolated and asexually reproduced by budding.

Among the novel characteristics possessed by this new variety which distinguish it from its parent and all other varieties of which I am aware are its attractive pink blend flowers borne on a floriferous plant with long stems and suitef for production of cut flowers under glass. The new variety can be reproduced through propagation by cuttings, grafting, budding and micropropagation.

Asexual reproduction by budding of the new variety as performed in Holland shows that the foregoing and other distinguishing characteristics come true to form and are established and transmitted through succeeding propagations.

BRIEF DESCRIPTION OF ILLUSTRATIONS

The accompanying illustrations show typical specimens of the vegetative growth and flowers of the new variety in different stages of development depicted in color as nearly true as it is reasonably possible to make the same in a color illustration of this character. Colors may vary depending upon growing conditions under different climate, soil, and cultivation conditions, and phenotypic expression may also vary with light and environmental conditions.

One of the accompanying illustrations shows cut flower form of the new variety and the other illustration shows details of the new rose variety.

DETAILED DESCRIPTION OF THE NEW VARIETY

The following is a detailed description of my new variety, with color terminology in accordance with The Royal Horticultural Society Colour Chart (R.H.S.C.C.) and horticultural terminology in accordance with standard terminology used in UPOV-approved horticultural guidelines. The terminology used in color description herein refers to plate numbers in the aforementioned color chart.

Parentage: Mutation of 'Ruidriko'.

Class: Hybrid tea.

As can be seen in the accompanying detail illustration there is shown the top of a compound three, five and seven leaflet leaves 1, 2 and 3 (5-leaflet leaf) and 4, respectively; a stem, 5; buds, 6 and 7; a flower, 8, about one-third open; and a flower, more fully open, unnumbered, shown between bud 6 and the one-third open flower 8. Also shown are flower stems 10, 11 and 12, with reproduction organs displayed. The other illustration shows cut flower form.

The following further horticultural observations were made of specimens grown under glass in Holland.

FLOWER

Blooming habit: Nearly continuous.

A. Bud:

(1) *Size.*—Medium.

(2) *Form.*—Broad obovate (shape of longitudinal section just before separation of sepals); urn-shaped after sepals part.

(3) *Color.*—As sepals divide, bud coloration exhibits near white petal reverse with light red/deep pink margins at petal edge, near 52A to B with occasional green streak.

(4) *Sepals.*—Longer than green bud, generally simple to slightly foliated near 144A.

(5) *Peduncle.*—Length — long, about 11 cm. Aspect — straight. Strength — erect, very strong. Color — medium green, near 137A to 137A to 137B.

B. Bloom:

*Flower.*—Large to very large size; viewed from above — irregularly rounded; viewed from side — (a) upper part of fully opened flower, flattened convex; (b) lower part of fully opened flower, flattened convex.

(1) *Size.*—Average size when fully expanded — about 12 to 15 cm, stem length about 100 cm.

(2) *Borne.*—Singly, one to a stem.

(3) *Form.*—High centered, exhibition type, spiral imbricated, outer petals roll under, some petals quill to points.

(4) *Petalage.*—Medium petaled under normal conditions — fully double about 27 petals; petaloids present.

(5) *Color.*—When sepals part and petals begin to unfurl, light red/deep pink coloration of petal top surface becomes visible, ranging from 57D to 58D; outer petals exhibit pink washing into white from petal edge toward petal bottom on petal upper surface; deep pink tones remain on petal edge on underside but pale off-white predominates on inner petals of upper surface until blooms age, when deep pink lightens to very pale pink. The pink coloration washes into the white background. Overall tonality from a distance is very attractive light red/deep pink with near white bicolor tones displayed as a pink blend.

(6) *Peduncle.*—Medium number of hairs or prickles.

(7) *Fragrance.*—Slight to none.

C. Petals:

(1) *Texture.*—Crisp.

(2) *Appearance.*—Inside velvety and outside satiny (3) *Form and size.*—First well developed outer petals — large, very broad, obovate.

(4) *Arrangement.*—Regularly arranged, imbricated.

(5) *Petaloids in center.*—Several.

(6) *Lasting quality.*—Long lasting quality on plant and after cutting, about 14 days after cutting and about 20 days on the plant; petals persist.

REPRODUCTIVE ORGANS

A. Stamens, filaments and anthers:

*Arrangement and color.*—Regularly arranged around styles; color filaments — red.

B. Pollen:

*Color.*—Deep yellow, near 19A.

C. Styles: Long, stigma above mouth of receptacle, red, slight to medium hairy.

D. Stigmas: Red, positioned below anthers.

E. Hip: Pitcher-shaped; large seed vessel at petal fall.

PLANT

A. Form: Narrow bushy, average disease resistance.

B. Growth: Vigorous, about 200 to about 250 cm.

C. Foliage: Compound 3, 5 and 7 leaflets.

(1) *Size.*—Very large.

(2) *Quantity.*—Abundant.

(3) *Color.*—Foliage at time of first flowering — light to medium green; juvenile foliage — red/-purple, near 178A depending on weather and method of cultivation; mature leaf color — near 136A, undersurface near 136C.

(4) *Shape.*—Oval, pointed.

(5) *Texture.*—Upper side is slightly glossy; underside is matte.

(6) *Edge.*—Serrate.

(7) *Serration.*—Ordinary, acuminate apices.

(8) *Leaf stem.* — Color — medium green, near 137A.

(9) *Stipules.*—Variable short to long, simple, medium green, distinct auricle.

(10) *Leaflets.*—Cross section — slight convex; none to very little undulation at margin; terminal leaflet — blade long and medium width, rounded base; petiole — medium.

D. Wood:

(1) *New wood.*—Color — young shoots have medium to strong anthocyanin, coloration — bronze to reddish brown near 178B.

(2) *Old wood.*—Color — medium green, near 147B.

E. Prickles (thorns):

(1) *Prickles.*—Present; quantity (main stalk) — ordinary; on laterals from stalk — ordinary; shape of lower side — concave. Length — significant. Color — between 147B and 184B. Position — irregular. Number $\leqq 5$ mm — very few. Number $\geqq 5$ mm — medium.

I claim:

1. A new and distinct variety of rose plant of the hybrid tea rose class, substantially as shown and described.

* * * * *

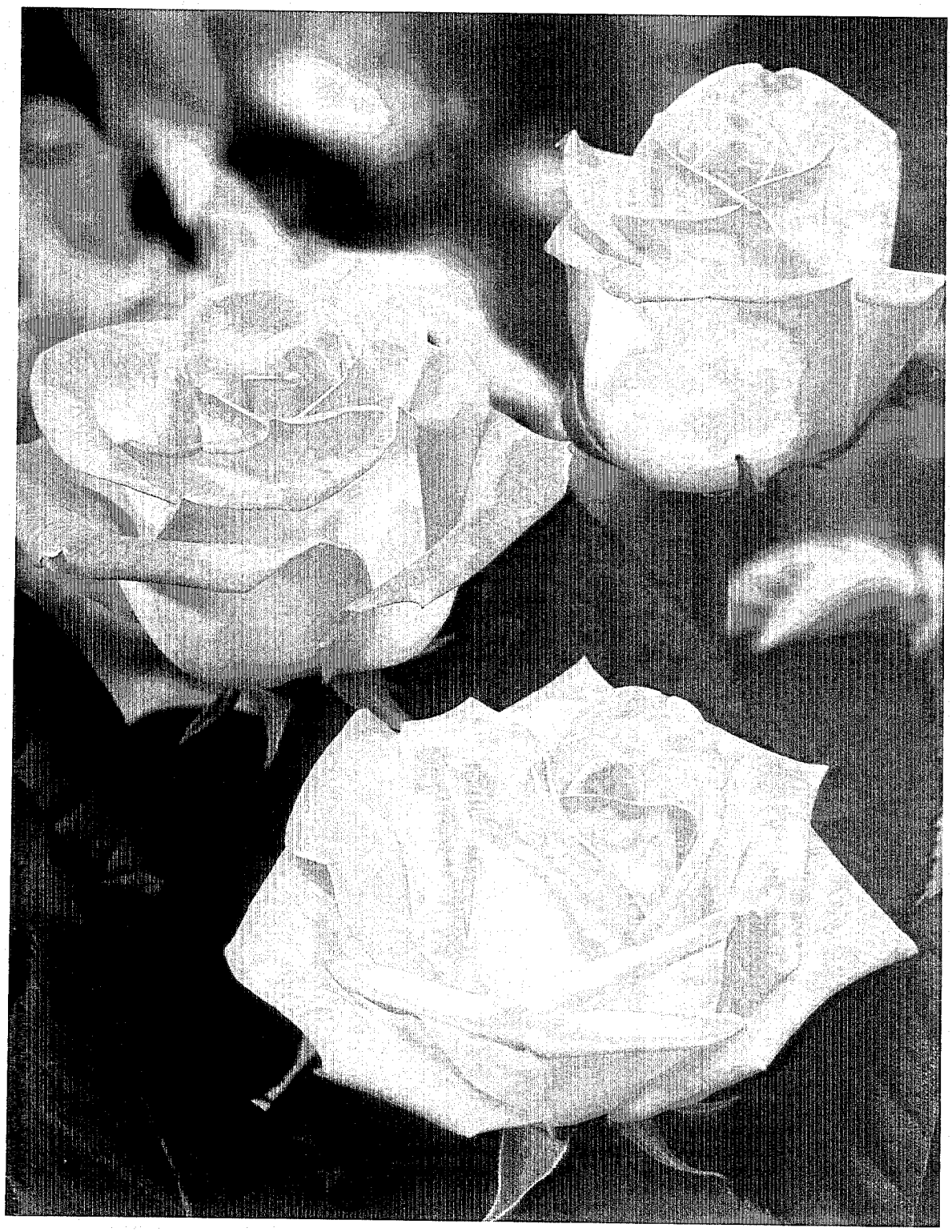

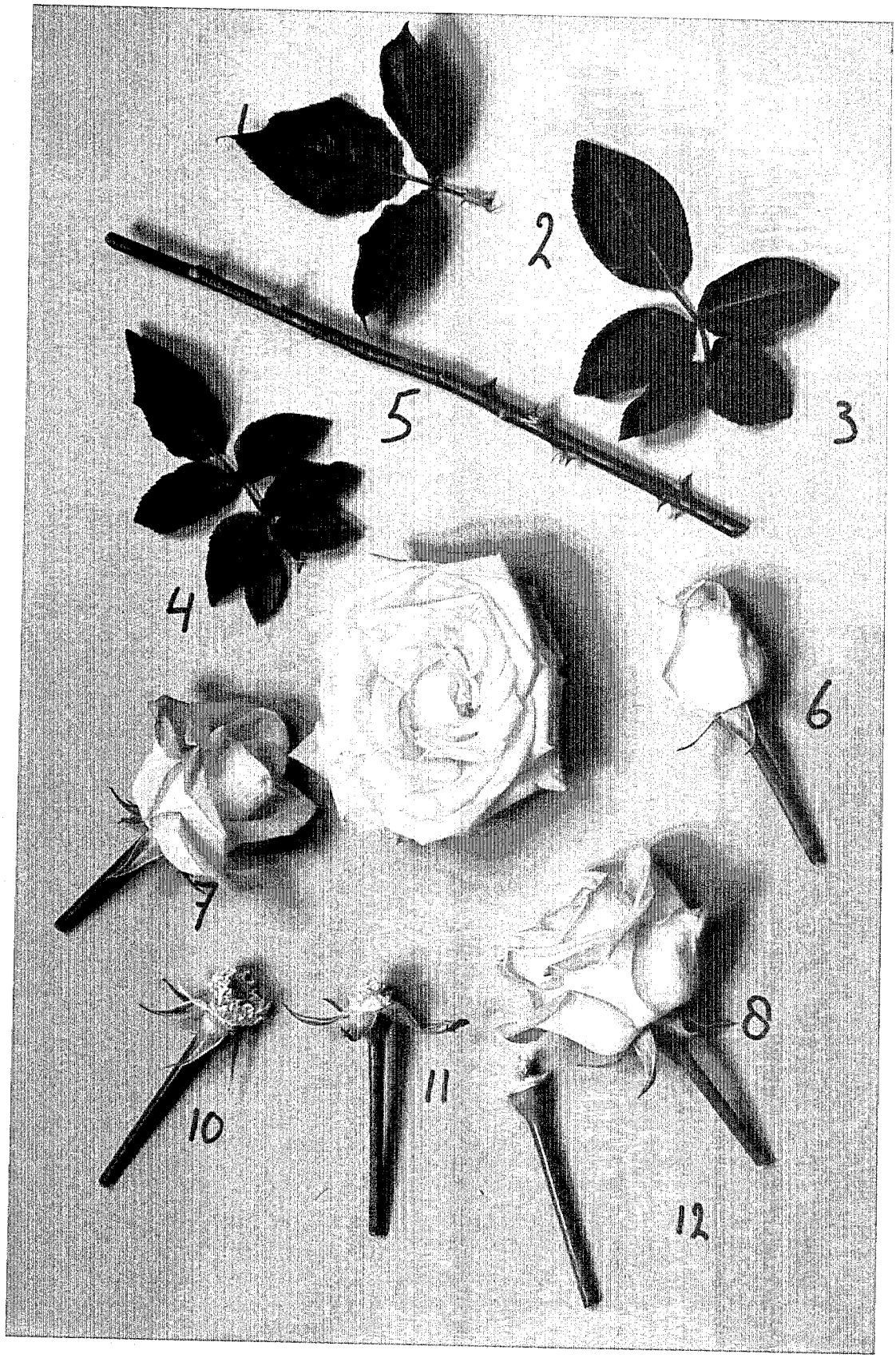
1
2
3
4
5
6
7
8
10
11
12

UNITED STATES PATENT AND TRADEMARK OFFICE

CERTIFICATE OF CORRECTION

PATENT NO. : Plant 9,198

DATED : July 18, 1995

INVENTOR(S) : W. M. van der Kooy

It is certified that error appears in the above-indentified patent and that said Letters Patent is hereby corrected as shown below:

Column 1, line 14, change "suitef" to -- suited --.
Column 1, line 47, change "description" to -- descriptions --.

Column 2, line 31, change "137A to 137A" to -- 137A --.
Column 2, 41, change "Forn" to -- Form --.

Signed and Sealed this

Twenty-eighth Day of January, 1997

*Attest:*

Bruce Lehman

BRUCE LEHMAN

*Attesting Officer*

*Commissioner of Patents and Trademarks*